United States Patent
Fulmer et al.

(10) Patent No.: US 6,486,365 B1
(45) Date of Patent: Nov. 26, 2002

(54) PRODUCTION AND PURIFICATION OF PHENOL: HYDROXYACETONE REMOVAL BY HYDROTALCITE

(75) Inventors: John W. Fulmer, Mt. Vernon, IN (US); Bharat Singh, Bangalore (IN); Pramod Kumbhar, Bangalore (IN); Prashant Anil Tatake, Maharashtra (IN); Umesh Hasyagar, Bangalore (IN)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 10/063,258

(22) Filed: Apr. 4, 2002

(51) Int. Cl.$^7$ ................................................ C07C 37/08
(52) U.S. Cl. ...................... 568/768; 422/189; 568/749; 568/754; 568/758
(58) Field of Search .................. 568/754, 758, 568/749, 768; 422/189

(56) References Cited

U.S. PATENT DOCUMENTS

| | | | |
|---|---|---|---|
| 3,335,070 A | | 8/1967 | Adams |
| 3,692,845 A | | 9/1972 | Cheema |
| 4,933,494 A | * | 6/1990 | Tubota |
| 5,008,470 A | | 4/1991 | Powell |
| 5,105,026 A | | 4/1992 | Powell |
| 5,358,701 A | | 10/1994 | Pinnavaia |
| 5,399,329 A | | 3/1995 | Schutz |
| 5,507,980 A | | 4/1996 | Kelkar |
| 6,066,767 A | | 5/2000 | Zakoshansky |
| 6,156,696 A | | 12/2000 | Albers |
| 6,313,063 B1 | | 11/2001 | Rytter |

FOREIGN PATENT DOCUMENTS

| | | |
|---|---|---|
| GB | 1108584 | 4/1968 |
| GB | 1381398 | 1/1975 |

* cited by examiner

Primary Examiner—Michael L. Shippen
(74) Attorney, Agent, or Firm—Oppedahl & Larson LLP

(57) ABSTRACT

A process for converting carbonyl-type impurities contained in a phenolic solvent to high-boiling derivatives is provided by contacting the phenolic solvent with a hydrotalcite-type material (HTM). The phenol can be separated from the high-boiling derivatives using conventional separation techniques, such as distillation, so the invention also provides a process for separating carbonyl-type impurities, such as hydroxyacetone (HA), from a phenolic solvent. The process can be applied in the conventional industrial process for converting cumene to phenol to remove carbonyl-type impurities from the phenol product. A process and a facility for producing purified phenol by converting cumene to phenol are provided. In the conversion of cumene to phenol, the phenol often contains carbonyl-type impurities. The phenol and carbonyl-type impurities are reacted in the presence of an HTM to produce phenol and high-boiling derivatives. The phenol may be further purified using conventional separation techniques, such as distillation, to remove the high-boiling derivatives.

72 Claims, 1 Drawing Sheet

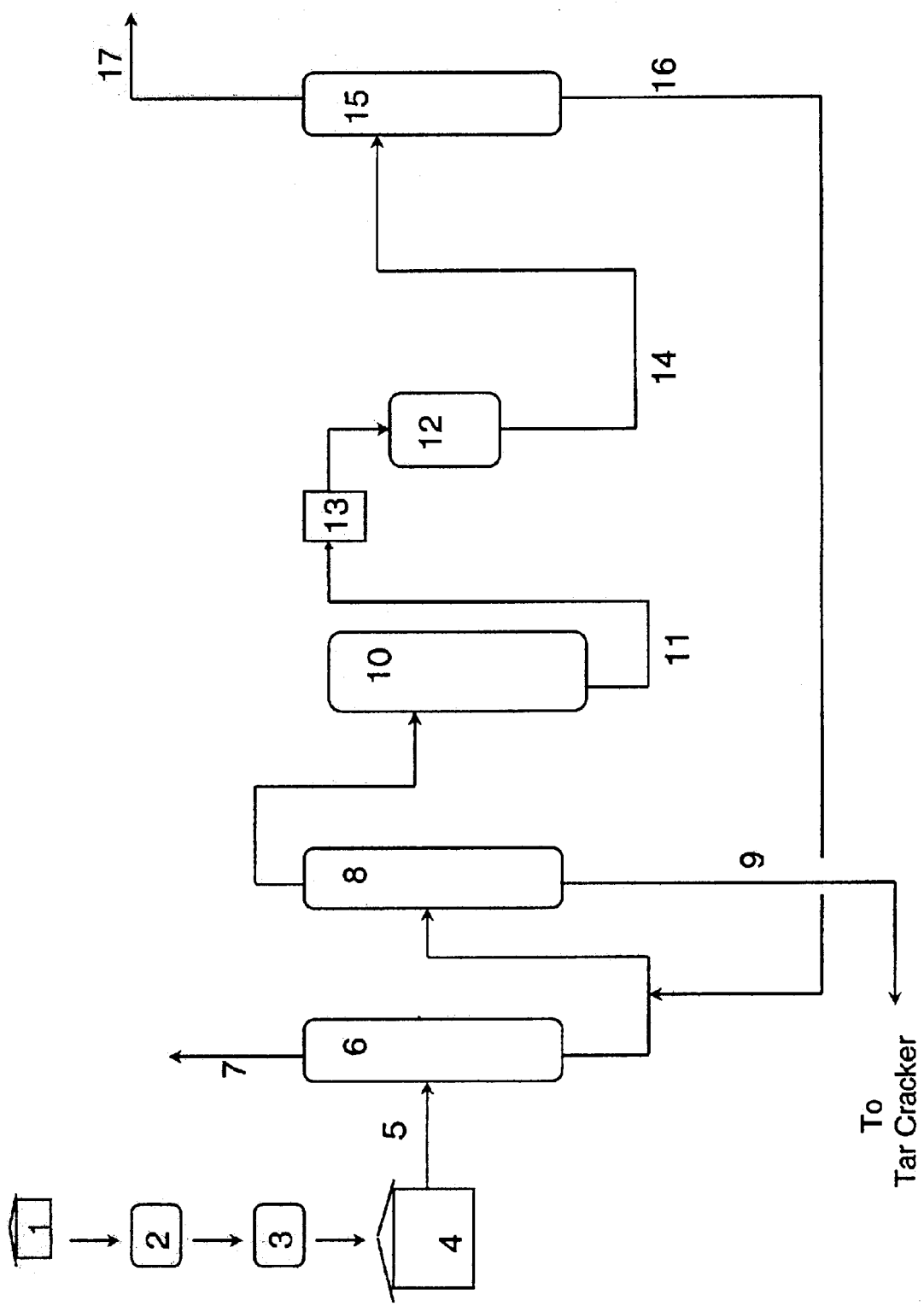

PRODUCTION AND PURIFICATION OF PHENOL: HYDROXYACETONE REMOVAL BY HYDROTALCITE

BACKGROUND OF INVENTION

The present invention relates to a method for production and purification of phenol.

The cumene-to-phenol industrial method is well known and involves a two step synthesis: air-oxidation of cumene to a cumene hydroperoxide (CHP) intermediate, followed by acidic decomposition (cleavage) of the CHP by contacting it with an acid catalyst such as sulfuric acid to yield phenol and acetone as principle products. However, in addition to the desired products, the resulting crude cleavage product mixture also contains amounts of various by-products including alpha-methylstyrene, acetophenone, cumylphenol, dimethylbenzyl alcohol, unreacted cumene and traces of various "carbonyl-type" impurities including hydroxyacetone, mesityl oxide and aldehydes. During the subsequent purification steps these undesirable by-products and impurities must be removed from the final product phenol and acetone using various separation methods which include extraction, distillation and catalytic chemical treatment.

The hydroxyacetone (HA) impurity is known to be produced at the CHP cleavage step via oxidation of acetone at concentrations of 1000 to 2500 ppm, depending on the operating conditions employed. When the CHP cleavage mixture, containing sulfuric acid catalyst, is neutralized, the HA present in the mixture equilibrates and partitions into the two phases in the neutralizer vessel in about equal concentrations. HA is particularly difficult to remove from phenol in the downstream process because it co-distills with phenol during the rectification processes and contaminates the final phenol product. The HA impurity has color-forming tendencies, so trace amounts of HA in the final product phenol renders the phenol product quality unacceptable for many end-use applications, such as bisphenol A and polycarbonate.

Since conventional distillation methods are not effective for removing HA from the phenol product, a number of various chemical treatment methods have been adopted in the industry to achieve its removal via condensation reactions and conversion to higher boiling materials that can be more easily separated from phenol in subsequent distillations. Both homogeneous and heterogeneous processes are described in the prior art. Those processes use both basic and acidic treating agents on the organic streams in the rectification area of the phenol process to promote HA condensation reactions, including sodium hydroxide, amines, ion exchange resins, and zeolites (U.S. Pat. Nos.: 3,335,070, 3,454,653, 3,692,845, 5,502,259, and 6,066,767). However, the use of the chemical treatment processes involving ion exchange resins, alumina, silica-alumina, and zeolites results in the reaction of HA and phenol to form a new impurity, 2-methylbenzofuran (2MBF), which is nearly impossible to separate from phenol by distillation at a product column, so phenol quality suffers. The maximum amount of 2MBF that can be present in the final product without significantly affecting the quality is 20 ppm. The amount of 2MBF formed with ion exchange resins is determined by the concentration of HA in the phenol stream supplied to the ion exchange resin. Typically, the use of ion exchange resins to purify phenol from HA results in the formation of 2MBF in amounts that affect the quality of the phenol product. Zeolites are generally superior to ion exchange resins with respect to catalyst life, but they typically generate even higher amounts of 2MBF.

The use of sodium hydroxide or amines as acidic treating agents on the organic streams in the rectification area of the phenol process to promote HA condensation reactions causes other problems. For example, the use of sodium hydroxide has been found to have the following disadvantages:

The strongly basic sodium hydroxide reacts with the phenol itself to form a sodium phenolate salt. This phenolate salt must be recovered or a loss in phenol yield will result;

The sodium phenolate salt can cause fouling of heat exchanger surfaces resulting in downtime and lost production; and The sodium phenolate salt can contaminate the final product phenol during the subsequent distillation process causing poor quality product and color.

The use of amines results in the production of waste phenol tar, among other things. The waste products are disposed of by burning, thus forming nitrogen oxides that are released into the atmosphere increasing pollution.

Therefore an improved method is needed for removing carbonyl-type impurities, such as HA, from phenol streams without introducing significant amounts of additional contaminants, such as 2MBF, or other by-products that can foul the machinery or increase pollution levels.

SUMMARY OF INVENTION

It has been discovered that layered double hydroxides (LDHS) can be effectively employed as catalysts that are useful in the process of converting carbonyl-type impurities, such as hydroxyacetone (HA), contained in a phenol stream into high-boiling derivatives that can be removed from the phenol stream by conventional separation techniques, such as distillation. Thus, in accordance with the invention, a process for converting carbonyl-type impurities, such as hydroxyacetone (HA), contained in a phenol stream into high-boiling derivatives is provided by contacting the phenolic solvent with a layered double hydroxide composition. Preferably, the LDH is a hydrotalcite-type material (HTM) of the formula:

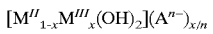

$[M^{II}_{1-x}M^{III}_{x}(OH)_2](A^{n-})_{x/n}$ or a hydrate thereof, wherein $M^{II}$ is a divalent metal cation, $M^{III}$ is a trivalent metal cation, A is an interlayer anion of charge n–, and x is from 0.12 to 0.8. The phenol can be separated from the high-boiling derivatives using conventional separation techniques, such as distillation, so the invention also provides a process for separating carbonyl-type impurities from a phenolic solvent. The process can be applied in the conventional industrial process for converting cumene to phenol to remove carbonyl-type impurities from the phenol product without introducing significant amounts of additional contaminants, such as 2MBF. A process and a facility for producing purified phenol by converting cumene to phenol are provided. In the conversion of cumene to phenol, the phenol often contains carbonyl-type impurities, such as HA. The phenol and carbonyl-type impurities are reacted in the presence of an HTM to produce high-boiling derivatives. The phenol may be further purified using conventional separation techniques, such as distillation, to separate it from the high-boiling derivatives.

BRIEF DESCRIPTION OF DRAWINGS

The drawing shows a diagram illustrating an embodiment of the invention process.

DETAILED DESCRIPTION

Surprisingly, it has been discovered that layered double hydroxides (LDHs) can be effectively employed as catalysts for converting carbonyl-type impurities, such as hydroxyacetone (HA), contained in a phenol stream into high-boiling derivatives that can be removed from the phenol stream by conventional separation techniques, such as distillation. LDHs are widely used in the industry as adsorbants, but they are not conventionally used for catalytic applications.

LDHs are a group of layered anionic clay minerals made up of positively charged layers of metal hydroxides, between which are located anions and some water molecules. Most common LDHs are based on double hydroxides of such main group metals as Mg and Al and transition metals, such as Ni, Co, Cr, Zn and Fe, etc. The structure of these LDHs is similar to that of brucite [Mg(OH)$_2$] in which the magnesium ions are octahedrally surrounded by hydroxyl groups with the resulting octahedra sharing edges to form infinite layers. In the LDHs, some of the Mg$^{2+}$ is isomorphously replaced by a trivalent cation, such as Al$^{3+}$. This results in a positively charged layer necessitating charge balancing by insertion of anions between the layers.

One type of LDH which has been found to be especially effective in the current inventive process is synthetic solid "hydrotalcite-type" material (HTM). True hydrotalcite is a rare naturally-occurring mineral having the idealized unit cell formula:

$$[Mg_6Al_2(OH)_{16}](CO_3) \cdot 4 H_2O$$

consisting of magnesium and aluminum hydroxide octahedrons interconnected via the edges. However, the ratio of Mg/Al can vary between 1.7 and 4 and various other divalent and trivalent ions may be substituted for Mg and Al. Additionally, the interlayer anion can be replaced in synthesis by a large number of other anions.

Hydrotalcite-type materials (HTMs) can be represented by the general formula:

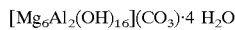

or a hydrate thereof, wherein M$^{II}$ is a divalent metal cation, M$^{III}$ is a trivalent metal cation, A is an interlayer anion of charge n−, and x is from 0.12 to 0.8. The preferable range for x is from 0.2 to 0.33. The M$^{II}$ is preferably selected from the alkaline earth metal cations alone or in combination with other divalent metal cations.

Preferably, M$^{II}$ is an alkaline earth metal cation. More preferably, M$^{II}$ is magnesium cation. The M$^{III}$ is preferably selected from the Group IIIA metal cations alone or in combination with other trivalent metal cations. Preferably, M$^{III}$ is a Group IIIA metal cation. More preferably, M$^{III}$ is aluminum cation. The HTMs can by commercially synthesized in large quantity by various methods. Their preparation is well known and described by Cavani, F. et al., *Cat Today*, Vol. 11, No. 2, p.173 (1991), and in U.S. Pat. Nos. 5,358,701, 5,399,329, 5,507,980, 6,156,696, and 6,313,063. The anion A is preferably selected from the group consisting of $CO_3^{2-}$, $NO_3^-$, $OH^-$, $Cl^-$, $F^-$, or combinations thereof. More preferably, the anion A is $CO_3^{2-}$. It will be appreciated by a person skilled in the art that various substitutions can be made for the interlayer anions including, but not limited to, simple anions, such as $SO_4^{2-}$, etc., transition metal anions, such as $CrO_4^{2-}$, $MoO_4^{2-}$, $Mo_2O_7^{2-}$, etc., organometallic anions, metal polyoxoanions, such as $V_{10}O_{28}^{6-}$, and organic anions, such as long chain aliphatic dicarboxylates. Methods effecting such substitutions are in the prior art, and such substituted products are within the scope of the present invention.

Preferable HTMs employed in the present invention are aluminum magnesium hydroxide carbonates which possess the general chemical formula:

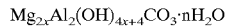

such as those produced commercially by Sasol-Condea under the trade name Pural MG and by Sudchemie under the trade name EXM, which can be expressed by the idealized formula:

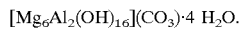

Compared to conventional alumina hydrates (pH 8–9) these anionic magnesium hydrotalcites are even more alkaline in nature and have a much higher surface area after calcination (400° C.: 200 m$^2$/gram) with corresponding increased catalytic activity. These HTMs can be used in an uncalcined or calcined form, however, the calcined form is more active due to its higher surface area. Their basicity is adjustable by increasing the Mg/Al ratio and/or incorporating anions other than OH$^-$. For example, a Mg/Al ratio of 3 results in a more basic material. Also, the material can be made less basic by incorporating Cl$^-$ instead of OH$^-$, or it can be made more basic by incorporating F$^-$) instead of OH$^-$.

These HTMs are thermally stable up to at least 500° C. giving them a wide temperature range of application. Further, these HTMs can be pelletized with good mechanical strength properties for long life catalytic and adsorptive utility in continuous-flow packed bed commercial applications. Examples 3 and 4 show that the HTM, upon being recycled, does not lose significant efficiency for catalyzing a reaction between HA and phenol to form high-boiling derivatives. The form and texture of the HTM is not critical to the present invention, and may vary depending on the type of preparation method, among other factors. However, it is preferred that the particle size be less than 5 mm. Preferably, the particle size range is from 1 mm to 3 mm. The HTM particles may be formed by conventional techniques, such as spray drying, pelletizing, tableting, bead formation and the like. Binders may be used to aid in the formation of particle shapes. Furthermore, these HTMs are stable in both aqueous and organic media without causing any leaching.

The present invention provides a process for converting carbonyl-type impurities, such as hydroxyacetone (HA), present in a phenolic solvent to high-boiling derivatives, by contacting the phenolic solvent with a catalyst at a catalytically-effective temperature thereby producing a phenol-containing stream with high-boiling derivatives and a reduced amount of carbonyl-type impurities, including HA. The catalyst is an HTM (as defined above). Typically, the catalytically-effective temperature at which the catalyst and phenolic solvent are contacted is from 40° C. to 400° C. Preferably, the catalytically-effective temperature at which the catalyst and phenolic solvent are contacted is from 200° C. to 300° C. More preferably, the catalytically-effective temperature is from 210° C. to 220° C. After the treatment, the phenol-containing stream contains no more than 20 ppm of 2MBF and no more than 1 ppm of HA. Preferably, the phenol-containing stream contains no more than 2 ppm of 2MBF and zero ppm of HA.

The present invention provides a process for separating carbonyl-type impurities, such as HA, from a phenolic solvent, by contacting the phenolic solvent with a catalyst at a catalytically-effective temperature, thereby producing a phenol-containing stream with high-boiling derivatives of the carbonyl-type impurities and with a reduced amount of carbonyl-type impurities including HA, and separating the high-boiling derivatives of the carbonyl-type impurities from the phenol-containing stream using conventional separation techniques. The catalyst is an HTM (as defined above). Typically, the catalytically-effective temperature at which the catalyst and phenolic solvent are contacted is from 40° C. to 400° C. Preferably, the catalytically-effective temperature at which the catalyst and phenolic solvent are contacted is from 200° C. to 300° C. More preferably, the catalytically-effective temperature is from 210° C. to 220° C. After the treatment, the phenol-containing stream contains no more than 20 ppm of 2MBF and no more than 1 ppm of HA. Preferably, the phenol-containing stream contains no more than 2 ppm of 2MBF and zero ppm of HA. The conventional separation techniques for purifying the phenol-containing stream include distillation, sorption, extraction, and phase separation.

The present invention further provides a process for producing phenol via the conversion of cumene to crude phenol. The crude phenol typically contains carbonyl-type impurities, such as HA. The crude phenol and any carbonyl-type impurities are reacted in the presence of a catalyst at a catalytically-effective temperature to produce a reaction product that contains phenol and may contain high-boiling derivatives of the carbonyl-type impurities and/or a small amount of 2MBF. The catalyst is an HTM (as defined above). Typically, the catalytically-effective temperature at which the crude phenol and any carbonyl-type impurities are reacted is from 40° C. to 400° C. Preferably, the catalytically-effective temperature at which the crude phenol and any carbonyl-type impurities are reacted is from 200° C. to 300° C. More preferably, the catalytically-effective temperature is from 210° C. to 220° C. After the treatment, the reaction product contains no more than 20 ppm of 2MBF and no more than 1 ppm of HA. Preferably, the reaction product contains no more than 2 ppm of 2MBF and zero ppm of HA. The reaction product may be further purified using conventional separation techniques, such as distillation, sorption, extraction, and phase separation, to isolate the phenol.

The present invention may be applied in the conventional industrial process for converting cumene to phenol, wherein a crude phenol stream (CPS) which may contain carbonyl-type impurities, such as HA, is produced. The improvement to that process comprises contacting the crude phenol stream containing carbonyl-type impurities, such as HA, with a catalyst at a catalytically-effective temperature to produce a phenol product containing high-boiling derivatives of the carbonyl-type impurities and less of the carbonyl-type impurities. The catalyst is an HTM (as defined above). Typically, the catalytically-effective temperature at which the catalyst and CPS are contacted is from 40° C. to 400° C. Preferably, the catalytically-effective temperature at which the catalyst and CPS are contacted is from 200° C. to 300° C. More preferably, the catalytically-effective temperature is from 210° C. to 220° C. After the treatment, the phenol product contains no more than 20 ppm of 2MBF and no more than 1 ppm of HA. Preferably, the phenol product contains no more than 2 ppm of 2MBF and zero ppm of HA. The treatment with an HTM can be effected using either a fixed or fluidized bed mode or using a slurry type application. A fixed bed design is preferable. Any method, such as batch mode or continuous mode, can be used. Following treatment with the catalyst, a high quality final product phenol can be recovered by conventional separation means, such as distillation, sorption, extraction, and phase separation.

The present invention also provides a facility for converting cumene to phenol. The facility comprises: a vessel containing cumene; a first reaction vessel connected to the vessel containing cumene, wherein in the first reaction vessel the cumene is oxidized to form a cumene hydroperoxide (CHP) mixture; a second reaction vessel connected to the first reaction vessel, wherein in the second reaction vessel the CHP mixture is cleaved to form a crude cleavage mass mixture; a third reaction vessel connected to the second reaction vessel, wherein in the third reaction vessel a base is added to the crude cleavage mass mixture to form a neutralized crude cleavage mass mixture; a separation section connected to receive the neutralized crude cleavage mass mixture, wherein the neutralized crude cleavage mass mixture is separated into streams, wherein one of those streams is a crude phenol stream (CPS) comprising phenol and which may contain carbonyl-type impurities, such as HA; a temperature control mechanism connected to receive the CPS; and a catalyst bed connected to receive the CPS after it passes through the temperature control mechanism. The temperature of the catalyst bed is controlled by the temperature control mechanism by either pre-heating or pre-cooling the CPS stream using a pre-heater or pre-cooler (heat exchanger). The catalyst bed comprises an HTM (as defined above). After passing through the catalyst bed, the CPS has a reduced amount of carbonyl-type impurities, including HA, and becomes a purified phenol-containing product. Typically, the temperature control mechanism can maintain a temperature of 40° C. to 400° C. in the catalyst bed. Preferably, the temperature control mechanism can maintain a temperature in the catalyst bed of 200° C. to 300° C. More preferably, the temperature control mechanism can maintain a temperature in the catalyst bed of 210° C. to 220° C. The purified phenol-containing product contains no more than 20 ppm of 2MBF. Preferably, the purified phenol-containing product contains no more than 2 ppm of 2MBF.

Some examples of bases that may be added to the crude cleavage mass mixture to form a neutralized crude cleavage mass mixture are sodium hydroxide, ammonia and organic amines.

The separation section may comprise a distillation apparatus, a sorption apparatus, a phase separation apparatus, an extraction apparatus, or a combination of these. Preferably, the separation section comprises one or more distillation apparatuses. More preferably, the separation section comprises three distillation columns in series.

The temperature control mechanism may comprise a thermocouple connected to a controller and a heating and/or a cooling element. The temperature in the catalyst bed is usually achieved by using a pre-heater/pre-cooler for the CPS feed. Most preferably, it is achieved by directly feeding the CPS from the separation section into the catalyst bed.

The facility may also comprise a second separation section connected to the catalyst bed, wherein the purified phenol-containing product is separated into two or more streams and wherein one of the streams is a phenol stream having greater purity than the purified phenol-containing stream. The second separation section may comprise a distillation apparatus, a sorption apparatus, a phase separation apparatus, an extraction apparatus, or a combination of these. Preferably, the second separation section comprises a distillation apparatus. More preferably, the second separation section comprises a single distillation column.

An embodiment of the process of the current invention as shown in the drawing is now described in more detail. By the conventional continuous flow cumene-to-phenol process, fresh cumene 1 is oxidized 2 to cumene hydroperoxide (CHP) and is subsequently cleaved 3 (acidic decomposition) to form a crude cleavage mass mixture containing phenol, acetone, unreacted cumene and the various byproducts formed including "carbonyl-type" impurities such as hydroxyacetone, aldehydes, and mesityl oxide. This crude cleavage mass mixture is neutralized 4 by addition of a base and then released as a stream 5 for further processing via the distillation columns (6, 8, 10). From these three distillation steps are continuously generated: A) a crude acetone stream 7, B) a tar stream 9, and C) a crude phenol stream 11. The crude phenol stream 11 consists of 97–99 wt % phenol containing a number of trace impurities including 100–200 ppm "carbonyl-type" contaminants which cannot be removed from phenol via conventional distillation.

The crude phenol stream 11 next passes continuously through a fixed-bed vessel 12 containing an HTM which effects a chemical removal of the "carbonyl-type impurities" present in the stream by acid-catalyzing their reaction with phenol to form high-boiling derivatives. The typical operating temperature of the fixed-bed vessel is 210–220° C. controlled by a temperature control mechanism 13, which pre-heats or pre-cools the CPS feed to the fixed-bed vessel. The effluent 14, essentially free of HA and other carbonyl-type impurities, feeds the final distillation column 15 where the high-boiling derivatives formed in the fixed-bed vessel 12 are removed via stream 16 from the final product phenol, stream 17. High quality final product phenol is produced suitable for bisphenol and polycarbonate plastics end use.

The HTMs can be regenerated by several methods as previously described in the art. A preferable method for regeneration involves washing the HTM with water, and then heating the HTM in nitrogen or air at 200° C. to 600° C. Heating at 400° C. is preferable.

The following non-limiting examples are provided for illustrative purposes only and should not be construed as limiting the scope of the present invention.

EXAMPLE 1

A synthetic mixture of phenol and HA (200–1000 ppm) was placed in an autoclave. The operating conditions maintained within the autoclave were 215° C., 500 rpm, and a 30 minute residence time. The HTM catalyst, PuralMg-70, in the form of a calcined powder (2% loading) was added to the autoclave. The HA conversion in the resulting HTM-treated reaction mixture was measured and found to be 96%. An amount of 1.5% of 2MBF (3 ppm–15 ppm) was found in the reaction mixture. This result shows that treatment with an HTM can be effective in reducing the amount of HA and with the formation of a low amount of 2MBF by-product from HA.

EXAMPLE 2

The method of Example 1 was repeated with the same raw materials, at the same operating conditions, but this time the HTM catalyst was PuralMg-70 pellets that had been crushed into a fine powder. The HA conversion in the resulting reaction mixture was found to be 94%, and 1.1% of 2MBF (2 ppm–11 ppm) was found in the reaction mixture.

EXAMPLE 3

The method of Example 2 was repeated at the same operating conditions, however, the HTM catalyst used was the one recovered from the experiment in Example 2. The HA conversion in the resulting reaction mixture was found to be 94%, and the amount of 2MBF was 0.2% (or less than 1 ppm–2 ppm). These results show that the catalyst is just as effective after being recycled once.

EXAMPLE 4

The method of Example 3 was repeated at the same operating conditions, however, the HTM catalyst used was the one recovered from the experiment in Example 3. The HA conversion in the resulting reaction mixture was found to be 94%, and the amount of 2MBF was 0.3% (or less than 1 ppm–3 ppm). These results show that the catalyst is just as effective after being recycled twice.

What is claimed is:

1. A process for converting carbonyl-type impurities present in a phenolic solvent to high-boiling derivatives, which process comprises contacting the phenolic solvent with a catalyst at a catalytically-effective temperature, said catalyst comprising a layered double hydroxide composition of the formula:

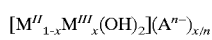

or a hydrate thereof, wherein $M^{II}$ is a divalent metal cation, $M^{III}$ is a trivalent metal cation, A is an interlayer anion of charge n–, and x is from 0.12 to 0.8, thereby producing a phenol-containing stream with high-boiling derivatives and a reduced amount of carbonyl-type impurities.

2. The process of claim 1, wherein the $M^{II}$ is selected from the alkaline earth metal cations alone or in combination with other divalent metal cations.

3. The process of claim 2, wherein the alkaline earth metal cation is magnesium cation.

4. The process of claim 1, wherein the $M^{III}$ is selected from the Group IIIA metal cations alone or in combination with other trivalent metal cations.

5. The process of claim 4, wherein the Group IIIA metal cation is aluminum cation.

6. The process of claim 1, wherein the anion A is selected from the group consisting of $CO_3^{2-}$, $NO_3^-$, $OH^-$, $Cl^-$, $F^-$, or combinations thereof.

7. The process of claim 1, wherein the anion A is $CO_3^{2-}$.

8. The process of claim 1, wherein x is from 0.2 to 0.33.

9. The process of claim 1, wherein the catalytically-effective temperature at which the catalyst and phenolic solvent are contacted is from 40° C. to 400° C.

10. The process of claim 1, wherein the catalytically-effective temperature at which the catalyst and phenolic solvent are contacted is from 200° C. to 300° C.

11. The process of claim 1, wherein the catalytically-effective temperature at which the catalyst and phenolic solvent are contacted is from 210° C. to 220° C.

12. The process of claim 1, wherein the phenol-containing stream contains no more than 20 ppm of 2-methylbenzofuran (2MBF).

13. The process of claim 1, wherein the phenol-containing stream contains no more than 2 ppm of 2MBF.

14. A process for separating carbonyl-type impurities from a phenolic solvent, which process comprises contacting the phenolic solvent with a catalyst at a catalytically-effective temperature, said catalyst comprising a layered double hydroxide composition of the formula:

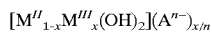

or a hydrate thereof, wherein $M^{II}$ is a divalent metal cation, $M^{III}$ is a trivalent metal cation, A is an interlayer anion of charge n−, and x is from 0.12 to 0.8, thereby producing a phenol-containing stream with high-boiling derivatives of the carbonyl-type impurities and with a reduced amount of carbonyl-type impurities, and separating said high-boiling derivatives of the carbonyl-type impurities from the phenol-containing stream using conventional separation techniques.

15. The process of claim 14, wherein the conventional separation technique is distillation.

16. The process of claim 14, wherein the $M^{II}$ is selected from the alkaline earth metal cations alone or in combination with other divalent metal cations.

17. The process of claim 16, wherein the alkaline earth metal cation is magnesium cation.

18. The process of claim 14, wherein the $M^{III}$ is selected from the Group IIIA metal cations alone or in combination with other trivalent metal cations.

19. The process of claim 18, wherein the Group IIIA metal cation is aluminum cation.

20. The process of claim 14, wherein the anion A is selected from the group consisting of $CO_3^{2-}$, $NO_3^-$, $OH^-$, $Cl^-$, $F^-$, or combinations thereof.

21. The process of claim 14, wherein the anion A is $CO_3^{2-}$.

22. The process of claim 14, wherein x is from 0.2 to 0.33.

23. The process of claim 14, wherein the catalytically-effective temperature at which the catalyst and phenolic solvent are contacted is from 40° C. to 400° C.

24. The process of claim 14, wherein the catalytically-effective temperature at which the catalyst and phenolic solvent are contacted is from 200° C. to 300° C.

25. The process of claim 14, wherein the catalytically-effective temperature at which the catalyst and phenolic solvent are contacted is from 210° C. to 220° C.

26. The process of claim 14, wherein the phenol-containing stream contains no more than 20 ppm of 2MBF.

27. The process of claim 14, wherein the phenol-containing stream contains no more than 2 ppm of 2MBF.

28. A process for producing phenol comprising the steps of:
converting cumene to produce a crude phenol which may contain carbonyl-type impurities;
reacting the crude phenol and any carbonyl-type impurities in the presence of a catalyst at a catalytically-effective temperature to produce a reaction product that contains phenol and may contain high-boiling derivatives of the carbonyl-type impurities and/or a small amount of 2MBF, said catalyst comprising a layered double hydroxide composition of the formula:

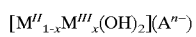

$$[M^{II}_{1-x}M^{III}_x(OH)_2](A^{n-})$$

or a hydrate thereof, wherein $M^{II}$ is a divalent metal cation, $M^{III}$ is a trivalent metal cation, A is an interlayer anion of charge n−, and x is from 0.12 to 0.8.

29. The process of claim 28, further comprising the step of separating the phenol from the reaction product using conventional separation techniques.

30. The process of claim 28, wherein the $M^{II}$ is selected from the alkaline earth metal cations alone or in combination with other divalent metal cations.

31. The process of claim 30, wherein the alkaline earth metal cation is magnesium cation.

32. The process of claim 28, wherein the $M^{III}$ is selected from the Group IIIA metal cations alone or in combination with other trivalent metal cations.

33. The process of claim 32, wherein the Group IIIA metal cation is aluminum cation.

34. The process of claim 28, wherein the anion A is selected from the group consisting of $CO_3^{2-}$, $NO_3^-$, $OH^-$, $Cl^-$, $F^-$, or combinations thereof.

35. The process of claim 28, wherein the anion A is $CO_3^{2-}$.

36. The process of claim 28, wherein x is from 0.2 to 0.33.

37. The process of claim 28, wherein the catalytically-effective temperature at which any carbonyl-type impurities and crude phenol are reacted is from 40° C. to 400° C.

38. The process of claim 28, wherein the catalytically-effective temperature at which any carbonyl-type impurities and crude phenol are reacted is from 200° C. to 300° C.

39. The process of claim 28, wherein the catalytically-effective temperature at which any carbonyl-type impurities and crude phenol are reacted is from 210° C. to 220° C.

40. The process of claim 28, wherein the reaction product contains no more than 20 ppm of 2MBF.

41. The process of claim 28, wherein the reaction product contains no more than 2 ppm of 2MBF.

42. In a process for converting cumene to phenol, wherein a crude phenol stream (CPS) which may contain carbonyl-type impurities is produced, the improvement comprising the step of contacting the CPS with a catalyst at a catalytically-effective temperature, thereby producing a phenol product that contains less of the carbonyl-type impurities, said catalyst comprising a layered double hydroxide composition of the formula:

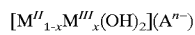

$$[M^{II}_{1-x}M^{III}_x(OH)_2](A^{n-})$$

or a hydrate thereof, wherein $M^{II}$ is a divalent metal cation, $M^{III}$ is a trivalent metal cation, A is an interlayer anion of charge n−, and x is from 0.12 to 0.8.

43. The process of claim 42, wherein the $M^{II}$ is selected from the alkaline earth metal cations alone or in combination with other divalent metal cations.

44. The process of claim 43, wherein the alkaline earth metal cation is magnesium cation.

45. The process of claim 42, wherein the $M^{III}$ is selected from the Group IIIA metal cations alone or in combination with other trivalent metal cations.

46. The process of claim 45, wherein the Group IIIA metal cation is aluminum cation.

47. The process of claim 42, wherein the anion A is selected from the group consisting of $CO_3^{2-}$, $NO^-$, $OH^-$, $Cl^-$, $F^-$, or combinations thereof.

48. The process of claim 42, wherein the anion A is $CO_3^{2-}$.

49. The process of claim 42, wherein x is from 0.2 to 0.33.

50. The process of claim 42, wherein the catalytically-effective temperature at which the catalyst and CPS are contacted is from 40° C. to 400° C.

51. The process of claim 42, wherein the catalytically-effective temperature at which the catalyst and CPS are contacted is from 200° C. to 300° C.

52. The process of claim 42, wherein the catalytically-effective temperature at which the catalyst and CPS are contacted is from 210° C. to 220° C.

53. The process of claim 42, wherein the phenol product contains no more than 20 ppm of 2MBF.

54. The process of claim 42, wherein the phenol product contains no more than 2 ppm of 2MBF.

55. A facility for converting cumene to phenol, said facility comprising:
a vessel containing cumene;
a first reaction vessel connected to the vessel containing cumene, wherein in said first reaction vessel the cumene is oxidized to form a cumene hydroperoxide (CHP) mixture;

a second reaction vessel connected to the first reaction vessel, wherein in said second reaction vessel the CHP mixture is cleaved to form a crude cleavage mass mixture;

a third reaction vessel connected to the second reaction vessel, wherein in the third reaction vessel a base is added to the crude cleavage mass mixture to form a neutralized crude cleavage mass mixture;

a separation section connected to receive the neutralized crude cleavage mass mixture, wherein the neutralized crude cleavage mass mixture is separated into streams, wherein one of those streams is a crude phenol stream (CPS) comprising phenol and which may contain carbonyl-type impurities;

a temperature control mechanism connected to receive the CPS; and a catalyst bed connected to receive the CPS, after it passes through the temperature control mechanism, and to produce a purified phenol-containing product, said catalyst bed comprising a layered double hydroxide composition of the formula:

$$[M^{II}_{1-x}M^{III}_{x}(OH)_2](A^{n-})$$

or a hydrate thereof, wherein $M^{II}$ is a divalent metal cation, $M^{III}$ is a trivalent metal cation, A is an interlayer anion of charge n−, and x is from 0.12 to 0.8.

56. The facility of claim 55, wherein the separation section comprises one or more distillation apparatuses.

57. The facility of claim 56, wherein the separation section comprises three distillation columns.

58. The facility of claim 55, wherein the temperature control mechanism can maintain a temperature in the catalyst bed of 40° C. to 400° C.

59. The facility of claim 55, further comprising a second separation section connected to the catalyst bed, wherein the purified phenol-containing product is separated into two or more streams wherein one of the streams is a phenol stream having greater purity than the purified phenol-containing stream.

60. The facility of claim 59, wherein the second separation section comprises a distillation apparatus.

61. The facility of claim 59, wherein the second separation section comprises a single distillation column.

62. The facility of claim 55, wherein the $M^{II}$ is selected from the alkaline earth metal cations alone or in combination with other divalent metal cations.

63. The facility of claim 62, wherein the alkaline earth metal cation is magnesium cation.

64. The facility of claim 55, wherein the $M^{III}$ is selected from the Group IIIA metal cations alone or in combination with other trivalent metal cations.

65. The facility of claim 64, wherein the Group IIIA metal cation is aluminum cation.

66. The facility of claim 55, wherein the anion A is selected from the group consisting of $CO_3^{2-}$, $NO_3^-$, $OH^-$, $Cl^-$, $F^-$, or combinations thereof.

67. The facility of claim 55, wherein the anion A is $CO_3^{2-}$.

68. The facility of claim 55, wherein x is from 0.2 to 0.33.

69. The facility of claim 55, wherein the temperature control mechanism can maintain a temperature in the catalyst bed of 200° C. to 300° C.

70. The facility of claim 55, wherein the temperature control mechanism can maintain a temperature in the catalyst bed of 210° C. to 220° C.

71. The facility of claim 55, wherein the purified phenol-containing product contains no more than 20 ppm of 2MBF.

72. The facility of claim 55, wherein the purified phenol-containing product contains no more than 2 ppm of 2MBF.

* * * * *